US 7,794,960 B2

United States Patent
Spector et al.

(10) Patent No.: US 7,794,960 B2
(45) Date of Patent: Sep. 14, 2010

(54) PREDICTIVE BIOMARKERS IN CANCER THERAPY

(75) Inventors: Neil Lee Spector, Durham, NC (US); Albert Man, La Jolla, CA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 448 days.

(21) Appl. No.: 11/569,980

(22) PCT Filed: May 12, 2005

(86) PCT No.: PCT/US2005/016470

§ 371 (c)(1),
(2), (4) Date: Dec. 4, 2006

(87) PCT Pub. No.: WO2005/121380

PCT Pub. Date: Dec. 22, 2005

(65) Prior Publication Data

US 2007/0190583 A1    Aug. 16, 2007

Related U.S. Application Data

(60) Provisional application No. 60/577,336, filed on Jun. 4, 2004.

(51) Int. Cl.
*G01N 33/53* (2006.01)
(52) U.S. Cl. .................... 435/7.23; 435/6; 436/501; 436/518
(58) Field of Classification Search ........................ None
See application file for complete search history.

(56) References Cited

U.S. PATENT DOCUMENTS

2003/0124130 A1    7/2003    Brown

2003/0152959 A1    8/2003    Mertz et al.

FOREIGN PATENT DOCUMENTS

WO    WO2004/000094    * 12/2003

OTHER PUBLICATIONS

Burris, H. The Oncologist, vol. 9, Suppl 3, 10-15, Jun. 3, 2004.*
Burris, Dual Kinase inhibition in the treatment of breast cancer: initial experience with the EGFR/ErB-2 inhibitor lapatinib, The Oncologist 9 (suppl):10-15 (2004).
Chakravarti et al., Insulin-like Growth Factor Receptor I Mediates Resistance to Anti-Epidermal Growth Factor Receptor Therapy in Primary Human Glioblastoma Cells through Continued Activation of Phosphoinositide 3-Kinse Signaling, Cancer Research 62:200-207 (2002).
Dudek et al, Regulation of Neuronal Survival by the Serine-Threonine Protein Kinase Akt, Science 275:661-665 (1997).
Koch et al., Pharmacokinetcs of GW572016 in an ascending does tolerability study of phase I cancer patients, European J. Cancer 1 Suppl 5):559a (2003) (Abstract).
Lu et al., Insulin-like Growth Factor-I Receptor Signaling and Resistance to Trastuzumab (Herceptin), Natl Cancer Inst 93(24):1852-1857 (2001).
Rusnak, et al., "The effects of the novel, reversible epidermal growth factor receptor/ErbB-2 tyrosine kinase inhibitor, GW2016, o nthe growth of human normal and tumor-derived cell lines in vitro and in vivo," 2001, Molecular Cancer Therapeutics 1:85-94 (2001).
Rusnak et al., The Characterization of Novel, Dual ErbB-2/EGFR, Tyrosine Kinase Inhibitors: Potential Therapy for Cancer, Cancer Research 61:7196-7203 (2001).
Spector et al., Proc Am Soc Clin Oncol 22:772 (2003) (Abstract).
Xia et al., Anti-tumor activit of GW572016: a dual tyrosine kinase inhibitor blocks EGF activation of EGFR/erbB2 and downstream Erk1/2 and AKT, Oncogene 21:6255-6263 (2002).
Zhou et al. "A Novel Strate of Colon Cancer Therapy: Targeting Both EGFR and ErbB2 Receptors." Proceedings of the American Association for Clinical Research, vol. 44, 2nd ed., Jul. 2003, p. 1101.

* cited by examiner

*Primary Examiner*—Misook Yu
(74) *Attorney, Agent, or Firm*—J. Scott Young

(57) ABSTRACT

The use of various biomarkers to assess a subject's suitability for treatment with a EGFR/ErbB2 kinase inhibitor for a solid tumor are described. The biomarkers include TGFalpha, pS6, IGF-1R and levels of apoptosis occurring in tumor tissue.

4 Claims, 4 Drawing Sheets

US 7,794,960 B2

PREDICTIVE BIOMARKERS IN CANCER THERAPY

CROSS-REFERENCE TO RELATED APPLICATIONS

This application is filed pursuant to 35 USC 371 as a United States National Phase Application of International Patent Application Serial No. PCT/US2005/016470 filed on May 12, 2005, which claims priority from 60/577,336 filed on Jun. 4, 2004 in the United States.

FIELD OF THE INVENTION

The present invention relates to biomarkers and methods of using the same in assessing the treatment of solid tumors with dual EGFR(erbB1)/erbB2 kinase inhibitors, or combined EGFR(erbB1) and erbB2 kinase inhibitors, and methods of identifying subjects suitable for such treatment.

BACKGROUND

Many existing anti-cancer chemotherapeutics are non-specific, in that they typically damage or kill normal cells as well as malignant cells. Research in oncology is increasingly focused on targeted therapies, in which a therapeutic compound interacts with a specific molecule to interfere with a particular molecular pathway. Tumors in different individuals, even when found at the same anatomic location, can differ in their molecular signalling pathways. Determining which molecules and pathways are affected by a therapeutic compound provides techniques to select patients suitable for treatment with that therapeutic, as well as provides methods of monitoring therapy in order to identify patients whose tumors are responding to the particular therapy in use.

ErbB Receptors

The ErbB family of type I receptor tyrosine kinases includes ErbB1 (also known as the epidermal growth factor receptor (EGFR or HER1)), ErbB2 (also known as Her2), ErbB3, and ErbB4. These receptor tyrosine kinases are widely expressed in epithelial, mesenchymal, and neuronal tissues where they play a role in regulating cell proliferation, survival, and differentiation (Sibilia and Wagner, *Science*, 269: 234 (1995); Threadgill et al., *Science*, 269: 230 (1995)). Increased expression of wild-type ErbB2 or EGFR, or expression of constitutively activated receptor mutants, transforms cells in vitro (Di Fiore et al., 1987; DiMarco et al, *Oncogene*, 4: 831 (1989); Hudziak et al., *Proc. Natl. Acad. Sci. USA.*, 84:7159 (1987); Qian et al., *Oncogene*, 10:211 (1995)). Increased expression of ErbB2 or EGFR has been correlated with a poorer clinical outcome in some breast cancers and a variety of other malignancies (Slamon et al., *Science*, 235: 177 (1987); Slamon et al., *Science*, 244:707 (1989); Bacus et al, *Am. J. Clin. Path.*, 102:S13 (1994)).

A family of peptide ligands binds to and activates ErbB receptor signaling, and includes epidermal growth factor (EGF) and transforming growth factor α (TGFalpha), each of which binds to EGFR (Reise and Stern, *Bioessays*, 20:41 (1998); Salomon et al., *Crit. Rev. Oncol. Hematol.*, 19: 183 (1995)). Ligand-receptor interactions are selective in that epidermal growth factor (EGF) and transforming growth factor alpha (TGFalpha) bind EGFR while heregulin binds ErbB3 and ErbB4. Ligand binding induces ErbB receptor phosphorylation (activation) with subsequent formation of homo- and heterodimers. ErbB2 is the preferred heterodimeric partner for EGFR, ErbB3, and ErbB4 (Graus-Porta et al., *EMBO J.*, 16:1647 (1997); Tzahar et al., *Mol. Cell. Biol.*, 16: 5276 (1996)). A number of soluble ligands have been identified for EGFR, ErbB3, and ErbB4, but none have been identified for ErbB2, which seems to be transactivated following heterodimerization (Ullrich and Schlessinger, *Cell*, 61: 203 (1990); Wada et al., *Cell*, 61: 1339 (1990); Karunagaran et al., *EMBO J.*, 15:254 (1996); Stern and Kamps, *EMBO J.*, 7: 995 (1988)).

ErbB1 and ErbB2 contain multiple tyrosine phosphorylation sites, and autophosphorylation of specific tyrosine residues within the highly conserved catalytic kinase domains of ErbB1 and ErbB2 establishes binding sites for Src-homology 2 (SH2) and phosphotyrosine-binding-domain containing proteins linking ErbB receptors to downstream cell proliferation (mitogen-activated protein kinase or MAPK; also known as Erk1/2) and survival (phosphatidylinositol-3-kinase or PI3K) pathways. Hackel et al: Curr Opin Cell Biol 11:184 (1999); Tzahar et al, Mol Cell Biol 16:5276 (1996); Lange et al. J Biol Chem 273:31308 (1998); Bacus et al., Oncogene 21:3532 (2002). Therapeutic modalities that target ErbB receptors and inhibit tyrosine kinase phosphorylation have been developed.

Therapeutics and ErbB2

Trastuzumab (Herceptin™), a humanized anti-ErbB2 monoclonal antibody has been approved for the treatment of breast cancers that either overexpress ErbB2, or that demonstrate ErbB2 gene amplification (Cobleigh et al, *J. Clin. Oncol.*, 17:2639 (1999)). Trastuzumab binds to the extracellular domain of the ErbB2 receptor, and has been reported to exert its antitumor effects through several mechanisms. See e.g., Sliwkowski et al., Semin. Oncol. 26(Suppl 12):60 (1999).

Gefitinib is a small molecule that targets and inhibits phosphorylation of EGFR (ErbB1). Gefitinib is approved for third-line treatment of non-small cell lung cancer.

Because heterodimers of ErbB2 and EGFR can elicit potent mitogenic signals, interrupting both ErbB2 and EGFR simultaneously is a potential therapeutic strategy (Earp et al., *Breast Cancer Res. Treat.*, 35:115 (1995)). Small molecule, dual EGFR-ErbB2 tyrosine kinase inhibitors have been identified and their pre-clinical anti-tumor activities reported (Fry et al., *Proc. Natl. Acad. Sci. USA*, 95:12022 (1998); Cockerill et al., *Bioorganic Med. Chem. Letts.*, 11:1401 (2001); Rusnak et al., *Cancer Res.*, 61:7196 (2001); Rusnak et al., *Mol. Cancer Therap.*, 1:85 (2001)).

GW572016 (lapatinib) is a potent reversible, dual inhibitor of the tyrosine kinase domains of both EGFR and ErbB2, with $IC_{50}$ values against purified EGFR and ErbB2 of 10.2 and 9.8 nM, respectively (Rusnak et al., *Mol. Cancer. Therap.*, 1:85 (2001)). Recent reports have demonstrated that lapatinib inhibits EGFR and ErbB2 autophosphorylation in tumor cell lines that overexpress these receptors (Rusnak et al., *Mol. Cancer. Therap.*, 1:85 (2001)), an effect that was primarily associated with tumor cell growth arrest. The chemical name of lapatinib (GW572016) is N-{3-chloro-4-[(3-fluorobenzyl) oxy]phenyl}-6-[5-({[2-methylsulfonyl)ethyl] amino}methyl)-2-furyl]-4-quinazolinamine (WO 99 35146, Carter et al.); a ditosylate form is disclosed in WO 02 02552 (McClure et al); methods of treating cancer are disclosed in WO 02/056912, and PCT/US03/10747.

It would be useful to identify biological molecules (biomarkers) that can be assessed, prior to therapy with a particular targeted therapy, to predict whether a tumor is likely to respond to that therapy. By screening subjects prior to therapy, those unlikely to respond to a given therapy can be treated with an alternate therapy. Similarly, it would be useful to identify biological molecules (biomarkers) that can be assessed during treatment with a particular targeted therapy, to indicate whether a tumor is responding to that therapy. By assessing such indicative biomarkers during therapy, resistance or non-response to a given therapy can be identified and an alternate therapy provided.

SUMMARY

Figures 1A, 1B:
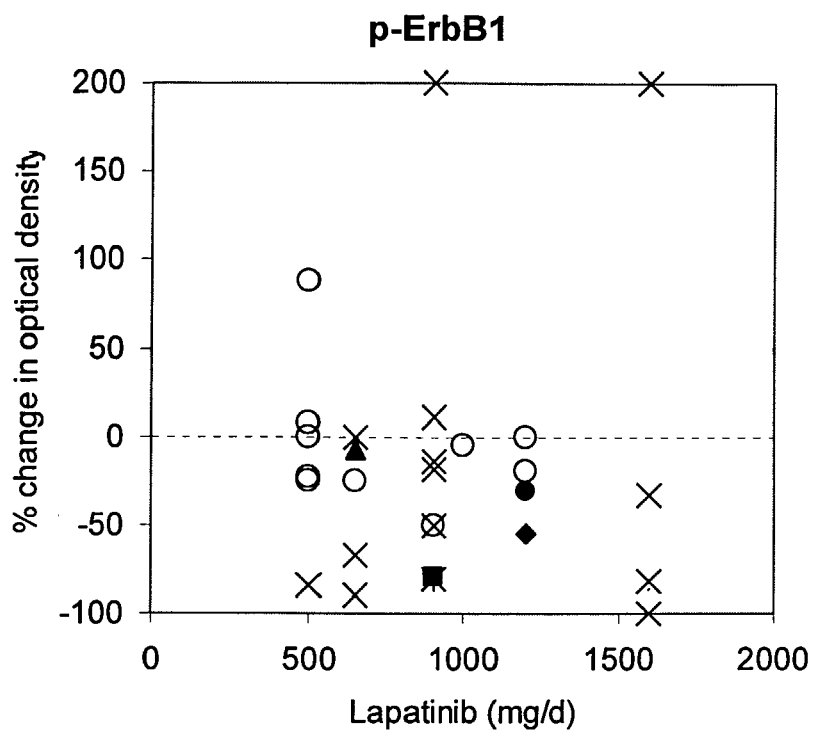
FIG. 1A graphs changes in pErbB1 (p-EGFR) as determined by comparing Day 0 and Day 21 tumor biopsies. Stable Disease (O), Progressive Disease (X), and four Partial Responses (▲, ●, ♦, ■) are indicated. A patient with PD despite marked inhibition of biomarkers (*) is also shown.
FIG. 1B graphs changes in pErbB2 as determined by comparing. Day 0 and Day 21 tumor biopsies. Stable Disease (O), Progressive Disease (X), and Partial Responses (▲, ●, ♦, ■) are indicated. A patient with PD despite marked inhibition of biomarkers (*) is also shown.
Figure 1C:
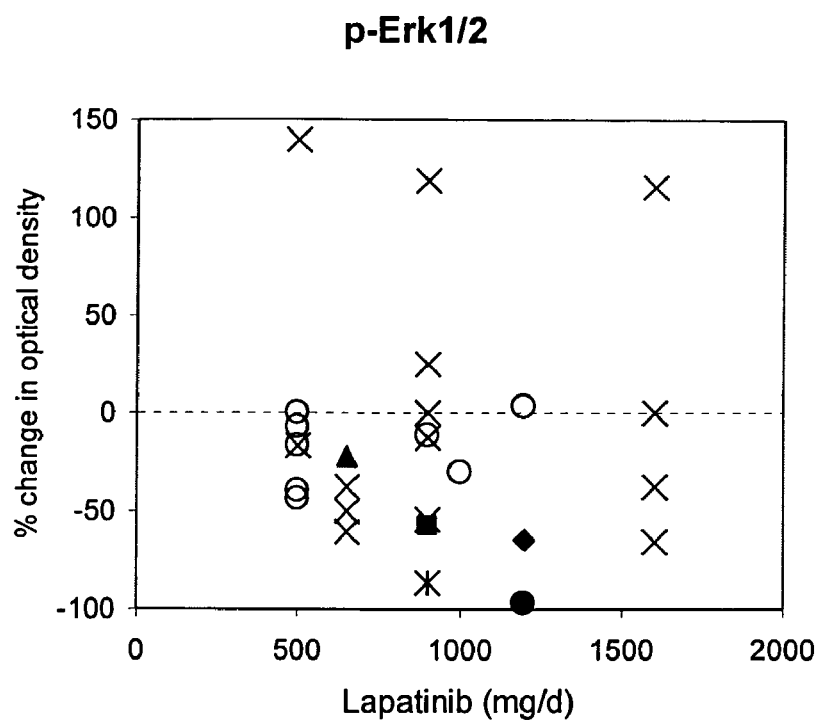
FIG. 1C graphs changes in pErk1/2 as determined by comparing Day 0 and Day 21 tumor biopsies. Stable Disease (O), Progressive Disease (X), and Partial Responses (Δ, ●, ♦, ■) are indicated. A patient with PD despite marked inhibition of biomarkers (*) is also shown.
Figure 1D:
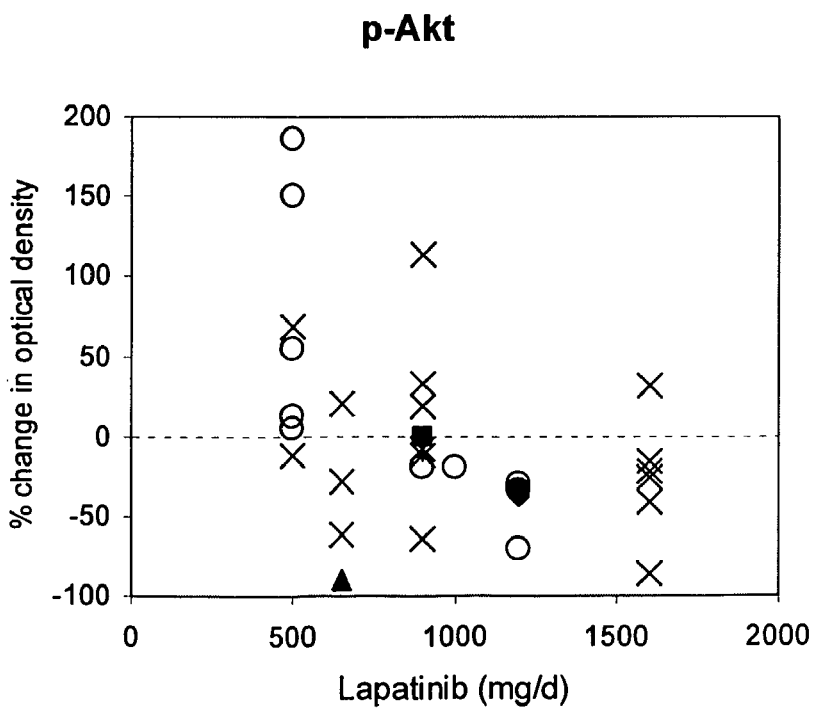
FIG. 1D graphs changes in pAkt as determined by comparing Day 0 and Day 21 tumor biopsies. Stable Disease (O), Progressive Disease (X), and Partial (▲, ●, ♦, ■) are indicated. A patient with PD despite marked inhibition of biomarkers (*) is also shown.
Figure 1E:
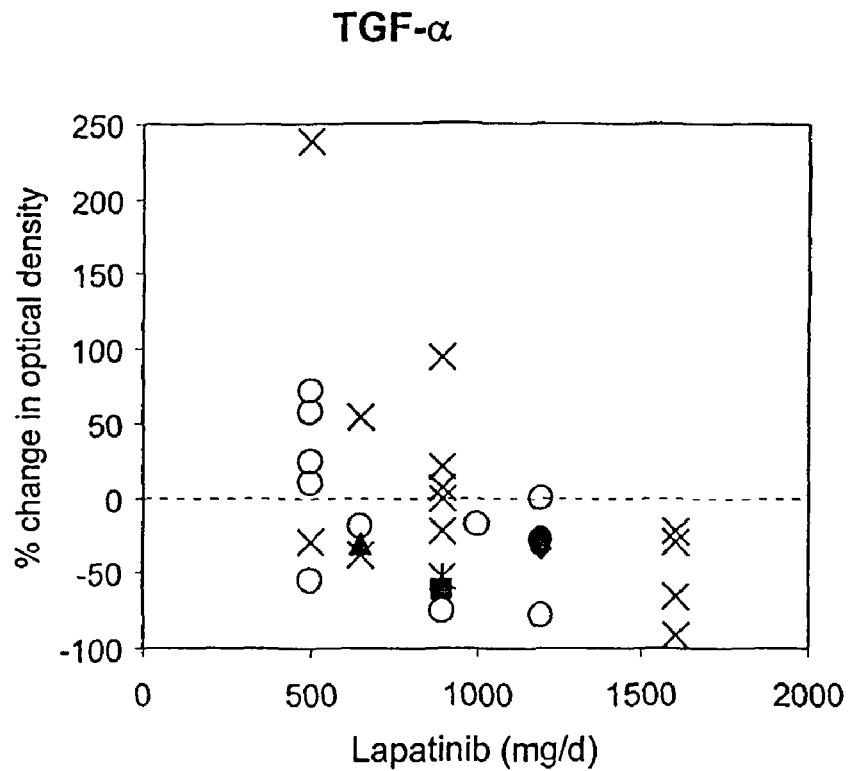
FIG. 1E graphs changes in TGFalpha as determined by comparing Day 0 and Day 21 tumor biopsies. Stable Disease (O), Progressive Disease (X), and Partial Responses (▲, ●, ♦, ■) are indicated. A patient with PD despite marked inhibition of biomarkers (*) is also shown.
Figure 1F:
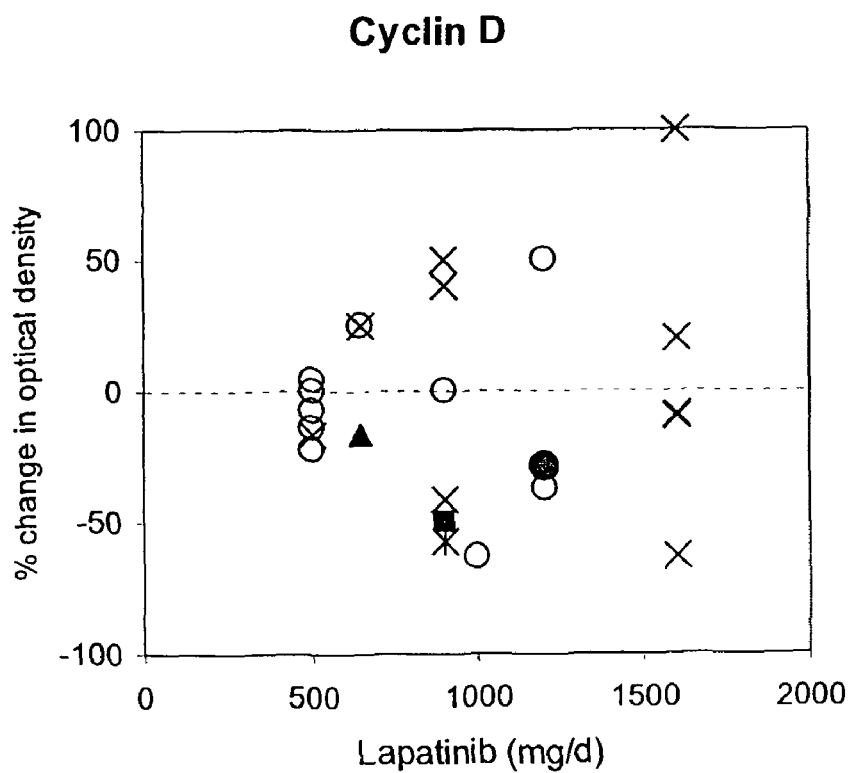
FIG. 1F graphs changes in Cyclin D as determined by comparing Day 0 and Day 21 tumor biopsies. Stable Disease (O), Progressive Disease (X), and Partial Responses (▲, ●, ♦, ■) are indicated. A patient with PD despite marked inhibition of biomarkers (*) is also shown.

One aspect of the present invention is a method of screening a human subject in need of treatment for a solid tumor, as an aid in selecting therapy. The method comprises determining whether the tumor expresses, or contains, increased levels of a biomarker selected from IGF-1R, TGFalpha and pS6. Increased pretreatment expression or levels of at least one of these markers indicates the subject is likely to respond favorably (clinical response) to treatment with a dual EGFR/ErbB2 inhibitor.

A further aspect of the present invention is a method of screening a subject in need of treatment for breast cancer to determine suitability for treatment with lapatinib. The method comprises determining whether said tumor expresses, or contains, increased pretreatment levels of a biomarker selected from IGF-1R, TGFalpha and pS6. Increased pretreatment expression indicates the subject is likely to respond favorably (clinical response) to treatment with lapatinib.

A further aspect of the present invention is a method of screening a human subject in need of treatment for a solid tumor, as an aid in selecting therapy. The method comprises determining whether the tumor has, prior to treatment with a dual EGFR/ErbB2 inhibitor, a minimal or undetectable level of apoptosis in the tumor tissue. A minimal or undetectable level of apoptosis indicates the subject is not likely to respond favorably (clinical response) to treatment with a dual EGFR/ErbB2 inhibitor.

A further aspect of the present invention is a method of screening a subject in need of treatment for breast cancer to determine suitability for treatment with lapatinib. The method comprises determining whether the tumor has a minimal or undetectable level of apoptosis prior to treatment with lapatinib, where a minimal or undetectable level of apoptosis indicates the subject is not likely to respond favorably (clinical response) to treatment with lapatinib.

A further aspect of the present invention is a method of assessing a human subject receiving treatment with a dual EGFR/ErbB2 inhibitor for a solid tumor. The method comprises determining whether the level of apoptosis in the tumor has increased, after an initial period of treatment with a dual EGFR/ErbB2 inhibitor, compared to the level of apoptosis present in the tumor prior to treatment with a dual EGFR/ErbB2 inhibitor. An increase in apoptosis indicates the subject is likely to respond favorably (clinical response) to treatment with that dual EGFR/ErbB2 inhibitor.

DETAILED DESCRIPTION

The present studies were carried out in order to elucidate the biologic effects of lapatinib on tumor growth/survival pathways, and to identify biomarkers that are correlated with the clinical response of patients with cancer to treatment with a compound that inhibits EGFR and ErbB2 receptor phosphorylation.

Due to the network of growth factor receptors, ligands, and downstream cell proliferation and cell survival effector molecules, inhibiting a specific receptor tyrosine kinase may not be an effective therapeutic strategy in all individuals with cancer, as various compensatory pathways may exist to overcome the specific therapeutic inhibition. Accordingly, it will be useful to identify biological markers that indicate in an individual subject, whether the subject's tumor is likely to respond favorably to a particular therapeutic compound. Additionally, where treatment with a particular therapeutic compound has been initiated, it will be useful to identify biological markers that indicate whether the subject's tumor is responding to that therapeutic compound. While tumor size or progression of disease has traditionally been used to determine whether an individual was responding to a particular therapy, use of molecular markers may allow earlier identification of responders and non-responders. Non-responders can be offered alternate therapy, and spared potential side effects of a therapy that is ineffective for their specific tumor type.

Lapatinib (GW572016) is reported to inhibit the activation of EGFR, ErbB2, Erk1/2, and AKT as well as reduces cyclin D protein in human tumor cell lines and xenografts (Xia et al., Oncogene 21:6255 (2002); Rusnak et al., Cancer Res. 61:7196 (2001); Rusnak et al., Cancer Therap. 1:85 (2001)). Currently in clinical trials, lapatinib has shown preliminary clinical activity in a number of pre-treated patients with metastatic cancers, most notably breast cancer (Burris, Oncologist, 9(Suppl 3):10 (2004); and unpublished data).

In the studies reported herein, heavily pre-treated patients with metastatic cancers overexpressing ErbB2 and/or expressing ErbB1 were randomized to one of five dose cohorts of lapatinib (GW572016), which was administered orally once daily continuously. The effects of lapatinib on pre-selected biomarkers were assessed in sequential tumor biopsies (initial biopsy at Day 0 before therapy started; subsequent biopsy after 21 days of therapy). Clinical response was assessed after 8 weeks of therapy. Non-parametric statistical analyses were used to identify biomarkers that were predictive or confirmatory of response to lapatinib in breast and non-breast cancers.

Sequential tumor biopsies from 33 patients were examined. Partial responses (PR) occurred in 4 patients with breast cancer and disease stabilization (SD) in 11 others with various malignancies. Clinical responders (patients with either PR or SD) exhibited variable inhibition of phospho-ErbB1, phospho-ErbB2, phospho-Erk1/2, phospho-Akt, cyclin D1, and transforming growth factor alpha (TGFalpha). These effects may be necessary for clinical response (PR or SD) but do not appear sufficient for clinical response, as some patients had disease progression despite marked biomarker inhibition. Conversely, increased TUNEL score in Day 21 tumors (compared to Day 0) only occurred in responding patients.

Tumor Apoptosis—Indicative and Predictive

The presently reported studies demonstrate that increased tumor cell apoptosis (assessed using TUNEL staining) at Day 21 (compared to tumor cell apoptosis at Day 0) was an indicator of response to lapatinib. None of the patients with Progressive Disease at 8 weeks had increased Day 21 TUNEL scores, even where the MAPK-Erk1/2 and PI3K-Akt pathways were inhibited at Day 21. Interestingly, patients with increased Day 21 TUNEL (compared to Day 0) and experiencing a positive clinical response also had higher pre-treatment TUNEL scores (compared to non-responders).

The present studies further indicate that the pre-treatment level of tumor apoptosis is predictive of response to treatment with a dual EGFR/ErbB2 agent such as lapatinib. All patients with high postdose TUNEL % had some pretreatment TUNEL %. Pretreatment TUNEL score provides an indication of the level of baseline tumor cell apoptosis. A baseline TUNEL score of 0 may indicate that the apoptotic pathway is not functional, which might be due to any of a variety of factors (e.g., inactivating mutations in effector caspases, selection of tumors with activated anti-apoptotic mediators-Bcl-2, heat shock proteins; see e.g., Pommier et al., Oncogene 23: 2934 (2004)). If the pro-apoptotic pathway in a tumor can not be activated, then tyrosine kinase inhibitors, which exert their anti-tumor effects by inducing apoptosis, will not be effective. The high incidence of tumors with baseline TUNEL scores of 0 in the current study may be an indication of the heavily pre-treated nature of the study population, where selective pressures for tumor survival favor cells with inoperative apoptotic machinery.

Predictive Biomarkers

Increased pre-treatment expression of IGF-IR, pS6, and TGFalpha were predictors of clinical response to lapatinib, especially in breast cancers. As used herein, an "increased" or "elevated" level of a biomarker may be defined as a level greater than the median level seen in subjects with the same histological tumor type; or alternatively as a level that has been determined to be predictive of clinical response to treatment with a particular therapy, whichever is appropriate as will be apparent to one skilled in the art. For any particular histological tumor type, the level of a particular biomarker that is correlated with positive clinical outcome can be determined by one skilled in the art, using methods known in the art.

Interestingly, while IGF-IR correlates for positive clinical response to lapatinib in the present studies, it has been reported as possibly mediating resistance to trastuzumab and gefitinib. (Chakravarti et al., Cancer Res 62:200 (2002); Lu et al, J Natl Cancer Inst 93:1852 (2001)). IGF-IR forms heterodimers with ErbB2. Signaling through IGF-IR/ErbB2 heterodimers appears to be hierarchical, with IGF-IR signaling being mediated through ErbB2 rather than vice versa. It is possible that high co-expression of IGF-IR and ErbB2 favors formation of ErbB2/IGF-IR complexes, whose signaling can be blocked by a potent ErbB2 kinase inhibitor such as lapatinib. Conversely, in the absence of high ErbB2 expression, IGF-IR may activate the PI3K-Akt-mTOR-p70S6K pathway through ErbB independent mediators such as IRS-1 and IRS-2, which would be insensitive to lapatinib. The relative expression of ErbB2 may therefore determine whether high pre-treatment levels of IGF-IR predicts for response or resistance to ErbB inhibitors.

In addition to ErbB receptors, ErbB receptor ligands expressed in many epithelial tumors through autocrine or paracrine mechanisms stimulate tumor proliferation and survival. Increased ligands in the tumor microenvironment activate their respective cognate receptors. One particular EGFR ligand, TGF alpha, has been implicated in the growth/survival of a variety of epithelial carcinomas. In the present study, increased pretreatment (Day 0) levels of TGFalpha were predictive for response to lapatinib. Expression of TGFalpha may indicate that an ErbB autocrine/paracrine loop is operative in the tumor and playing a role in regulating growth and survival signals, which would be sensitive to lapatinib.

The Present Methods

The present studies have identified biomarkers that, in patients with cancer and particularly in patients with breast cancer, are predictive of response to treatment with a dual EGFR/ErbB2 inhibitor such as lapatinib, or treatment with a combination of EGFR inhibitor and ErbB2 inhibitor. As used herein, a biomarker that is predictive of response to therapy is one whose pretreatment level is correlated with clinical response of the tumor to treatment. The correlation may be to a positive clinical response (e.g., partial response or stable disease), or to a negative clinical outcome (e.g., progressive disease).

The present invention provides methods of assessing a subject's tumor to identify whether the tumor is likely to respond favorably to treatment with a dual EGFR/ErbB2 inhibitor such as lapatinib, or treatment with a combination of EGFR inhibitor and ErbB2 inhibitor, by measuring the pre-treatment levels of IGF1-R, pS6 and/or TGFalpha. Increased levels of these biomarkers are correlated with positive clinical response. In a particularly preferred method of the present invention, the subject is afflicted with breast cancer.

Additionally, the present invention additionally provides a method of assessing a subject's tumor to identify whether the tumor is likely to respond favorably to treatment with a dual EGFR/ErbB2 inhibitor such as lapatinib, or treatment with a combination of EGFR inhibitor and ErbB2 inhibitor, by measuring the pre-treatment level of apoptosis in the tumor tissue. Minimal or undetectable levels of apoptosis are correlated with negative clinical response (resistance to therapy). In a particularly preferred method of the present invention, the subject is afflicted with breast cancer. In one embodiment of the present invention, a level of apoptosis equal to a score of less than about 30%, 20% or 10% using standard TUNEL assay is considered 'minimal'.

The present invention additionally provides methods of assessing a subject's tumor to identify whether the tumor is responding to treatment with a dual EGFR/ErbB2 inhibitor such as lapatinib, or treatment with a combination of EGFR inhibitor and ErbB2 inhibitor, by assessing the change in apoptosis in tumor tissue (comparing pre-treatment apoptosis to the apoptosis occurring after an initial period of treatment). An increase in tumor apoptosis is correlated with a positive clinical response. In a particularly preferred method of the present invention, the subject is afflicted with breast cancer.

Apoptosis may be assessed by any suitable method as will be apparent to one skilled in the art. Re-assessment "after an initial treatment period" refers to a period sufficient to allow the therapeutic agent to physically reach the site of the tumor, for a period sufficient to allow a biological response to the therapeutic agent in the tumor tissue. In one embodiment of the present invention, the initial treatment period is that period of time required for the therapeutic agent to reach steady-state plasma concentration (or shortly thereafter). Preferably the re-assessment of biological markers occurs shortly after the initial treatment period and prior to the end of a course of therapy, so that therapy may be discontinued in subjects who are not likely to respond. However, re-assessment may also be conducted at or immediately following the end of a course of therapy, to determine if the subject would be suitable for a second course of the same therapy, if required.

The methods of the present invention are suitable for use in subjects afflicted with a solid tumor, preferably of epithelial origin. Methods of the present invention are particularly suitable for use in subjects afflicted with breast cancer.

DEFINITIONS

As used herein, a method of screening or assessing a subject as an aid in predicting the subject's response to a therapeutic treatment, or in identifying a subject as suitable for a particular therapy, should not be confused with the use of disease prognosis markers. Certain molecular markers are known as indicators of more aggressive cancers and are associated with decreased average survival time (compared to subjects whose tumors do not express such markers). The present invention is not directed to general disease prognosis markers, but to the use of specified biological markers to assess an individual's potential for response to a therapeutic treatment, and to select treatment suitable for that individual's disease.

Methods of the present invention are directed to the screening of subjects with solid tumors, to identify those who are likely to respond more favorably to treatment with a dual ErbB2/EGFR inhibitor (or treatment with combined ErbB2 and EGFR inhibitors), compared to the response that would be expected from treatment without such inhibitors. More specifically, the methods of the present invention are directed to the screening of tumor tissue from a subject to identify whether that subject is likely to respond more favorably to treatment with dual or combined ErbB2/EGFR inhibitor(s), compared to the response that would be expected from treatment without dual or combined ErbB2/EGFR inhibitor(s).

More specifically, methods of the present invention are directed to assessing pretreatment levels of IGF-1R, pS6 and TGFalpha in a subject's tumor, where that subject is being considered for treatment of a solid tumor (particularly breast cancer) with a dual EGFR/ErbB2 tyrosine kinase inhibitor, or combined ErbB2/EGFR inhibitors. Subjects having elevated levels of IGF-1R, pS6 and/or TGFalpha, are considered to be more likely to exhibit a favorable clinical response to treatment with a therapeutic regime that includes dual or combined ErbB2/EGFR inhibitor(s), compared to subjects whose tumors do not express elevated levels of these biomarkers.

As used herein, methods to "predict" a favorable clinical response, or to "identify" suitable subjects, is not meant to imply a 100% predictive ability, but to indicate that subjects with certain characteristics are more likely to experience a favorable clinical response to a specified therapy than subjects who lack such characteristics. However, as will be apparent to one skilled in the art, some individuals identified as more likely to experience a favorable clinical response will nonetheless fail to demonstrate measurable clinical response to the treatment.

As used herein, a subject refers to a mammal, including humans, canines and felines. Preferably subjects treated with the present methods are humans.

As used herein, a 'favorable response' (or 'favorable clinical response') to an anticancer treatment refers to a biological or physical response that is recognized by those skilled in the art as indicating a decreased rate of tumor growth, compared to tumor growth that would occur with an alternate treatment or the absence of any treatment. "Favorable clinical response" as used herein is not meant to indicate a cure, but may indicate a Partial Response or Stable Disease. A favorable clinical response to therapy may include a lessening of symptoms experienced by the subject, an increase in the expected or achieved survival time, a decreased rate of tumor growth, cessation of tumor growth (stable disease), regression in the number or mass of metastatic lesions, and/or regression of the overall tumor mass (each as compared to that which would occur in the absence of therapy).

According to one embodiment of the present methods, biomarker levels are assessed assessed immediately before the subject begins a course of anti-neoplastic therapeutic treatment (pre-treatment). As used herein, 'immediately' before treatment refers to a biologically relevant time frame. Preferably the assessment is done within about three months, two months, or six weeks prior to treatment, more preferably within about four weeks, three weeks, two weeks, ten days or less prior to treatment. Alternatively in the methods of the present invention, the level of the specified marker may be assessed after treatment has begun, to ascertain whether the appropriate treatment is being used.

As is known in the art, clinical use of an antineoplastic agent typically involves repeated administration of the agent to a subject over a set time period, on a pre-established schedule. Therapeutic agents may be administered in any suitable method, including but not limited to intravenously (intermittently or continuously) or orally. For example, a 'course' of a certain therapeutic agent may require daily administration of the agent for two weeks; a course of therapy using a different therapeutic agent or for a different tumor type may involve once weekly administration for six weeks. As used herein, a "course" of therapy refers to a therapeutic schedule (dosage, timing of administration, and duration of therapy) that is specific to the therapeutic agent being used and/or the tumor type being treated, and that is accepted in the art as therapeutically effective. Such schedules are developed using pharmacologic and clinical data, as is known in the art. A subject may undergo multiple courses of treatment over time, using the same or different therapeutic agents, depending on whether disease progression occurs.

The present methods are suitable for use in subjects undergoing their first course of antineoplastic treatment, or subjects who have previously received a course of antineoplastic treatment for a tumor.

As is well known in the art, tumors are frequently metastatic, in that a first (primary) locus of tumor growth spreads to one or more anatomically separate sites. As used herein, reference to "a tumor" in a subject includes not only the primary tumor, but metastatic tumor growth as well.

As used herein, an ErbB2 inhibitor is an agent that inhibits or reduces the formation of p-Tyr/ErbB2 (activated ErbB2), compared to the formation of p-Tyr/ErbB2 that would occur in the absence of the ErbB2 inhibitor. Such inhibitors include small chemical molecules and biologic agents such as monoclonal antibodies. As used herein, an EGFR inhibitor is an agent that inhibits or reduces the formation of pTyr/EGFR (activated EGFR) compared to the formation of pTyr/EGFR that would be formed in the absence of the agent. Such inhibitors include small chemical molecules and biologic agents such as monoclonal antibodies.

As used herein, a cell "overexpressing" ErbB2 refers to a cell having a significantly increased number of functional ErbB2 receptors, compared to the average number of receptors that would be found on a cell of that same type. Overexpression of ErbB2 has been documented in various cancer types, including breast (Verbeek et al., *FEBS Letters* 425:145 (1998); colon (Gross et al., *Cancer Research* 51:1451 (1991)); lung (Damstrup et al., *Cancer Research* 52:3089 (1992), renal cell (Stumm et al, *Int. J. Cancer* 69:17 (1996), Sargent et al., *J. Urology* 142: 1364 (1989)) and bladder (Chow et al., *Clin. Cancer Res.* 7:1957 (2001); Bue et al., *Int. J. Cancer*, 76:189 (1998); Turkeri et al., *Urology* 51: 645 (1998)). The DAKO HercepTest® (DakoCytomation, Denmark), is an FDA approved IHC assay for the evaluation of ErbB2 protein overexpression, and provides semi-quantitative results of $p185^{ErbB2}$ overexpression by light microscopy. Samples are scored as from 0 (no staining, negative), 1+ (weak staining, negative), 2++ (weakly positive) and 3+++ (strongly positive). Typically patients with 2++ or 3+++ results are considered to be overexpressing ErbB2 and thus suitable for treatment with trastuzumab. Accordingly, a cell that 'overexpresses' ErbB2 is one that would score 2++ or 3+++ on the HercepTest®, or achieve a comparable score using another assay.

As used herein, "solid tumor" does not include leukemia or other hematologic cancers.

As used herein, an "epithelial tumor" is one arising from epithelial tissue.

As used herein, "breast cancer" refers to cancers arising in the mammary tissue, whether in males or females, and including ductal carcinoma in situ (also known as intraductal carcinoma), lobular carcinoma in situ, invasive (or infiltrating) ductal breast cancer, invasive (or infiltrating) lobular carcinoma, and inflammatory breast cancer (IBC).

Inhibitors of ErbB2 used in the present methods should preferentially inhibit phosphorylation of tyrosine residues within the kinase domain, which are the residues implicated in regulating downstream MAPK/Erk and PI3K/AKT pathways.

Immunohistochemistry

Immunohistochemistry is a staining method based on immunoenzymatic reactions using monoclonal or polyclonal antibodies to detect cells or specific proteins such as tissue antigens. Typically, immunohistochemistry protocols include detection systems that make the presence of the markers visible (to either the human eye or an automated scanning system), for qualitative or quantitative analyses. Various immunoenzymatic staining methods are known in the art for detecting a protein of interest. For example, immunoenzymatic interactions can be visualized using different enzymes such as peroxidase, alkaline phosphatase, or different chromogens such as DAB, AEC or Fast Red.

The methods of the present invention may be accomplished using any suitable method or system of immunohistochemistry, as will be apparent to one skilled in the art, including automated systems, quantitative IHC, semi-quantitative IHC, and manual methods.

As used herein, "quantitative" immunohistochemistry refers to an automated method of scanning and scoring samples that have undergone immunohistochemistry, to identify and quantitate the presence of a specified biomarker, such as an antigen or other protein. The score given to the sample is a numerical representation of the intensity of the immunohistochemical staining of the sample, and represents the amount of target biomarker present in the sample. As used herein, Optical Density (OD) is a numerical score that represents intensity of staining. As used herein, semi-quantitative immunohistochemistry refers to scoring of immunohistochemical results by human eye, where a trained operator ranks results numerically (e.g., as 1, 2 or 3).

Various automated sample processing, scanning and analysis systems suitable for use with immunohistochemistry are available in the art. Such systems may include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.).

Where phosphorylated proteins are being assayed, tissue must be processed in a manner that allows accurate detection of phosphorylated proteins. E.g., if the tissue sample is paraffin-embedded, it may be fixed in the presence of phosphatase inhibitors and in a neutralized buffered formalin solution.

Measurement of Apoptosis

Most animal cells can self-destruct via an intrinsic program of cell death characterized by specific morphologic and biochemical properties (apoptosis); apoptosis can be triggered by extracellular or intracellular signals. Disregulations of programmed cell death may contribute to diseases, for example, cancer and neurodegenerative diseases.

Various methods of detecting apoptosis exist. A commonly used method is TUNEL (Terminal deoxynucleotidyl Transferase Biotin-dUTP Nick End Labeling). One of the characteristics of apoptosis is the degradation of DNA after the activation of Ca/Mg dependent endonucleases. This DNA cleavage leads to strand breaks within the DNA. The TUNEL method identifies apoptotic cells in situ by using terminal deoxynucleotidyl transferase (TdT) to transfer biotin-dUTP to the free 3'-OH of cleaved DNA. The biotin-labeled cleavage sites are then visualized by reaction with fluorescein conjugated avidin (avidin-FITC). TUNEL apoptosis detection kits are commercially available (e.g., Upstate Biotechnology Inc., Charlottesville Va.;

Additional methods for the detection of apoptotic cells and specific parts of the apoptotic pathway are also available, such as the detection of caspase activity (e.g., caspase-3), fas-ligand and annexin V. Any suitable method for measurement of apoptosis in tumor tissue may be used in the methods of the present invention.

IGF1R

IGF-1R, the type 1 receptor for insulin-like growth factor, mediates cell survival and growth in response to its ligands IGF-1 and IGF-2. This tyrosine kinase receptor is widely expressed in many cell types and is a key mediator of growth. IGF-1R activates three signaling pathways that converge to phosphorylate BAD protein and block apoptosis. The first pathway activated by IGF-1R stimulates the PI3K/AKT/p70 ribosomal protein S6 kinase pathway to phohsphorylate BAD and promote proliferation. (Dudek et al., *Science*, 275:661 (1997)). A second pathway activated by IGF-1R involves ras-mediated activation of the map kinase pathway to block apoptosis. A third pathway involves interaction of raf with mitochondria in response to IGF-1R activation. The convergence of these pathways to block apoptosis may enhance the IGF-1R response. Any suitable method of detecting and measuring levels of IGF-1R in tumor tissue may be used in the methods of the present invention.

pS6

Ribosomal protein s6 (S6) is part of the small ribosomal sub-unit. It binds to the 18S rRNA early in the assembly pathway leading to the 40S ribosome. When cells are stimulated with growth factors and/or hormones, S6 is phosphorylated by the kinase p70S6K. Phosphorylation of ribosomal protein S6 by p70S6K stimulates the translation of mRNAs that encode components of the protein synthesis pathway. Any suitable method of measuring levels of pS6 in tumor tissue may be used in the methods of the present invention.

TGFalpha

Transforming Growth Factors (TGFs) are biologically active polypeptides that reversibly confer the transformed phenotype on cultured cells. TGFalpha shows about 40% sequence homology with epidermal growth factor and competes with EGF for binding to HER1, stimulating its phosphorylation and producing mitogenic response. Any suitable method of measuring levels of TGFalpha in tumor tissue may be used in the methods of the present invention.

The present methods are suited for use with any form of ErbB2/EGFR inhibitors, including organic molecules such as lapatinib, monoclonal antibodies, or other chemical or biological therapeutic agents. Specific inhibitors, as well as processes of making thereof, are provided in U.S. Pat. No. 6,169,091; U.S. Pat. No. 6,174,889; U.S. Pat. No. 6,207,669; U.S. Pat. No. 6,391,874; WO 99/35146; WO 01/04111.

Example 1

Subjects and Methods

Clinical Study Design

The Institutional Review Boards at the Sarah Cannon Cancer Center, University of North Carolina-Chapel Hill/Lineberger Comprehensive Cancer Center, Duke University Medical Center, and Case Western Reserve Medical Center approved this study. Patients providing informed consent were enrolled on this open-label, randomized trial if their tumors (i) overexpressed ErbB2 and/or ErbB1 (2+ to 3+ IHC staining in >10% of tumor cell, or (ii) demonstrated ErbB2 gene amplification by FISH. Additional eligibility criteria included the following: age ≧18 years; measurable metastatic solid malignancies not amenable to established standard therapies; Karnofsky performance status ≧70; no prior chemo-, radio-, hormonal or immunotherapy within the previous 4 weeks; LVEF ≧40%; Hgb ≧9 g/ml; ANC ≧1,500/mm$^3$; platelet ≧100,000/mm$^3$; total bilirubin ≦2.0 mg/dL and transaminases ≦3×ULN unless due to tumor.

Patients were randomized to one of five dose cohorts of lapatinib (500, 650, 900, 1,200, or 1,600 mg) administered orally, once daily on a continuous basis until evidence of disease progression or intolerable side effects. Of 67 patients enrolled in this study, 33 had evaluable Day 0 (pre-treatment) and Day 21 (post-treatment) tumor biopsy samples; see Tables 1A, 1B and 1C for additional Patient Characteristics of these 33 patients.

TABLE 1A

Patient Characteristics

| | No. of Patients | | | | |
|---|---|---|---|---|---|
| | Dose 500 mg | Dose 650 mg | Dose 900/1000 mg | Dose 1200 mg | Dose 1600 mg |
| Sex | | | | | |
| Male | 2 | 3 | 3 | 1 | 2 |
| Female | 5 | 3 | 7 | 3 | 4 |
| Age, years | | | | | |
| Median | 49 | 61 | 58 | 54.5 | 53 |
| Range | 28–68 | 53–82 | 42–82 | 46–64 | 38–58 |
| No. prior treatments | | | | | |
| Median | 7 | 7.5 | 4 | 3.5 | 6 |
| Range | 0–10 | 2–11 | 0–13 | 2–14 | 4–8 |
| Disease Site | | | | | |
| Breast | 4 | 1 | 5 | 3 | 1 |
| (ER+) | (1) | (0) | (1) | (0) | (1) |
| (PR+) | (2) | (1) | (3) | (1) | (0) |
| (ErbB2 2–3+) | (2) | (1) | (5) | (3) | (1) |
| (EGFR+) | (3) | (1) | (3) | (3) | (1) |
| (Prior herceptin Rx) | (2) | (1) | (4) | (3) | (1) |
| AUP | 0 | 1 | 2 | 0 | 0 |
| CRC | 1 | 1 | 1 | 0 | 1 |
| H&N | 0 | 1 | 0 | 1 | 2 |
| Ovarian | 0 | 1 | 1 | 0 | 1 |
| Lung | 0 | 1 | 1 | 0 | 0 |
| Other | 2 | 0 | 0 | 0 | 1 |

AUP = adenocarcinoma of unknown primary;
CRC = colorectal cancer
H&N = head and neck carcinoma
ER+ = estrogen receptor positive;
PR+ = progesterone receptor positive

TABLE 1B

Clinical Results by anatomic tumor type - all subjects

| Tumor Type | Number of Patients Enrolled | Partial Response (PR) | Stable Disease (SD) |
|---|---|---|---|
| Breast | 30 | 4 | 10 |
| Colon | 7 | 0 | 2 |
| Lung | 11 | 0 | 6 |
| Carcinoma of Unknown Primary | 5 | 0 | 5 |
| Ovarian | 4 | 0 | 2 |
| Head and Neck | 5 | 0 | 3 |
| Other | 5 | 0 | 4 |
| Total | 67 | 4 | 32 |

TABLE 1C

Description of Patients with Partial Response

| | Number of Patients |
|---|---|
| Dose of Lapatinib | |
| 650 mg/day | 1 |
| 900 mg/day | 1 |

TABLE 1C-continued

Description of Patients with Partial Response

| | Number of Patients |
|---|---|
| 1200 mg/day | 2 |
| ErbB2+ | 4 |
| ErbB1+ | 4 |
| Prior Treatment | |
| Trastuzumab | 4 |
| Taxane | 3 |
| Anthracycline | 3 |
| Response Duration | |
| Median | 5+ months |
| Range | 3.5–6+ months |

Tumor biopsies were obtained within 3 days prior to initiating lapatinib (day 0) and again on day 21, within 4 to 12 hours after administration of lapatinib. Patients were monitored by physical examination, clinical chemistry and hematology blood tests, and formally re-staged after 8 weeks of therapy. RECIST criteria were used to assess clinical response in appropriate target lesions (Therasse et al., New guidelines to evaluate the response to treatment in solid tumors. *J Natl Cancer Inst* 92:205 (2000)). Response was classified as Complete Response (CR), Partial Response (PR), Stable Disease (SD) or Progressive Disease (PD). Patients with CR, PR or SD were considered to have a positive clinical response. Patients with Progressive Disease (PD) were considered to have a negative clinical response.

Patients with a positive response to treatment (CR, PR or SD) continued on therapy with re-staging every 8 weeks thereafter. Patients were withdrawn from study upon evidence of disease progression or intolerable side effects.

Reagents

Anti-ErbB1, ErbB2, and cyclin D antibodies were purchased from Ventana Medical Scientific Instruments/VMSI (Tucson, Ariz.); anti-p-Akt (Ser 437) and p-Erk1/2 antibodies from Cell Signaling Technology Inc. (Beverly, Mass.); anti p-ErbB1 antibodies from Chemicon (Temecula, Calif.) and anti-transforming growth factor α (TGFalpha, IGF-IR, and p-ErbB2 antibodies from NeoMarkers (Fremont, Calif.); anti-Erk1/2 antibodies from Santa Cruz Biotechnology (Santa Cruz, Calif.).

Immunohistochemistry (IHC)

Biopsies were fixed in 10% neutral buffered formalin (NBF) and paraffin-embedded sections prepared. Hematoxylin and eosin (H&E) staining was used to confirm for the presence of tumor.

Established quantitative IHC assays were performed in a CLEA certified, CAP (College of American Pathologists) reference laboratory as previously described (Bacus et al., Analyt Quant Cytol Histol 19: 316 (1997)). ErbB1, ErbB2, and cyclin D1 immunostaining was performed using VMSI automated "BenchMark" staining module (Malik et al., Clin Cancer Res 9: 2478 (2003); Bacus et al., Analyt Quant Cytol Histol (1997)). The VMSI "I-View" detection kit was used for all three of the VMSI pre-diluted primary antibodies. Erk1/2 (1:1200), and TGFalpha (1:20) were immunostained using the "BenchMark" with I-VIEW detection chemistry. Phospho-Erk1/2 (1:100) and p-Akt (1:75) were immunostained using a labeled streptavidin peroxidase technique. Phospho-Erk1/2 and p-Akt slides were antigen retrieved as described (Bacus et al., *Analyt Quant Cytol Histol* 19:316 (1997)). Slides were placed onto the Autostainer (Dako, Carpinteria, Calif.) and used the labeled streptavidin-biotin peroxidase method (LSAB2 kit, Dako) as the detection chemistry. After staining, ErbB1, ErbB2, Erk1/2, p-Akt, p-Erk1/2, p-ErbB1, p-ErbB2, cyclin D1, IGF-IR, and TGFalpha were counterstained manually with 4% ethyl green (Sigma-Aldrich). TUNEL assay (Roche Diagnostics, Indianapolis, Ind.) was performed according to the manufacturer's instructions. Investigators preparing and analyzing tissue sections were blinded to both patient tumor type and response to therapy. ErbB2 OD values of $\leq 10$, 10 to 15, $\geq 15$ roughly correlate with 1+, 2+, 3+ in the HercepTest® standards, respectively.

Statistical Analysis

Results were analyzed with non-parametric tests due to the limited size and the uncertainty of normal distribution in some of the samples. Enhanced Pathological Analysis (EPA) measurement values and differences, and ratios were compared for patients who responded and those who did not, as assessed by response duration, post treatment clinical status, and post-treatment TUNEL %. Descriptive statistics, including mean and SD, median, lower quartile, upper quartile, minimum and maximum, were calculated for all sample measurements. Wilcoxon rank sum test and Kruskal-Wallis one-way analysis of variance by ranks were used to study changes in assayed proteins and TUNEL score. Spearman rank correlation was used to test the associations between outcome data and pre-treatment and post-treatment measurements. Univariate and multivariate discriminate analyses were performed to test the association between pre- and post-treatment measurements and patient outcome classes. In the discriminate analysis, the degree of concordance between predicted and observed binary class outcomes (identical to the area under the receiver operating characteristic (ROC) curve) was used as a measure of the predictive value of the discriminate models. All statistical tests were two sided and $P<0.05$ was considered statistically significant.

Example 2

Subjects and Sequential Tumor Biopsy Specimens

Demographics of the 33 patients are shown in Table 1. Expression of ErbB1, ErbB2, p-ErbB1, p-ErbB2, Erk1/2, p-Erk1/2, Akt, p-Akt, TGFalpha, IGF-IR and cyclin D1 was assessed by IHC with automated image analysis using established assays; OD values were assigned to each specimen. TUNEL scores represent the percent tumor cells staining positive. Day 21 biopsy specimens were obtained within 4 to 12 hours following lapatinib dosing to maximize the probability of detecting a biological response. Clinical responses, safety profile, and pharmacokinetics for this study have been previously reported (Spector et al., Proc Am Soc Clin Oncol 22: 772a (2003); Koch et al., Eur J Cancer 1 (suppl 5): 559a (2003)).

Example 3

Statistical Analysis

This study analyzed Phase I clinical trial data, analyzed in two subsets (Breast Cancer and Not Breast Cancer). The outcome measures were: clinical status, response duration, and postdose TUNEL %. The Clinical Status was either: Partial Response (PR), Stable Disease (SD), or Progressive Disease (PD). The Response Duration was valued at between 2 and 10 for SD or PR, and valued at 0 for Progressive Disease. The Postdose TUNEL % was used for classification, with TUNEL %>30 utilized as an indication of apoptosis.

The dataset included patient demographics, dose of lapatinib, measurements of nine different proteins, and TUNEL (predose, postdose and % change). The nine proteins (EGFR/ErbB1, ErbB2, ERK, AKT, TGFalpha, IGF1R, ribosomal protein S6, Heregulin (NDF), and cyclin D1). Some proteins were assayed in the phosphorylated state (pAKT), while EGFR/ErbB1 and ErbB2 were measured in both phosphorylated and unphosphorylated states.

The statistical methods employed were Correlation Analysis, Analysis of Variance, Fisher Discriminate Analysis and Receiver Operator Curve Scoring.

The measurement set was mined for significant relationships that described various outcome measures. First, monotonic or strong relationships were sought using correlation analysis. These relationships have substantial credibility even in small sample sets. Correlation analysis was also applied to identify significant but weaker relationships between the measurement set and the outcome set, as well as to identify relationships within the measurement set. These relationships while not strictly monotonic, and with less distinct correlations are still good indicators of important factors. Complimenting the correlation analysis, an analysis of variance (ANOVA) was performed to determine what variables of the measurement set were distinctly different when grouped by the various outcome measures. This allowed relationships to be identified that may not have a monotone relationship, but instead are effectively describing different outcome measure populations and thus may be useful for predicting or confirming various outcome measures. Receiver operator curves (ROC), defined as a plot of 1-specificity (false positive rate) vs. sensitivity (true positive rate) were calculated using the variables of the measurement set for various outcome measures. This analysis allows for greater outliers than either the correlation analysis for the ANOVA, and is useful to identify non-deterministic relationships, and for scoring the classifications identified and substantiated by other methods. The areas under receiver operator curves (AUC) were computed using a trapezoidal method to score how well univariate solution could solve various posed classification problems. Subsequently, multivariate discriminate analysis was performed and the resulting solution was scored by calculating the area under the respective receiver operator curves to identify the degree the interaction effects between members of the measurement set could improve the classification of the different outcomes over the univariate ROC AUC scores.

Correlation Analysis

Due to the small data set, sample set size and likely complex relationships between the variables, a nonparametric (distribution-free) rank correlation statistic was employed to measure the strength of the associations between paired variables. The Spearman rank correlation coefficient was used to give an estimate of Rs, the rank correlation coefficient, and the associated significance of the putative correlation. The rank correlation coefficient, Rs, is a measure of monotone association that is used when the distribution of the paired variables make the more common Pearson's correlation coefficient Rp undesirable or misleading.

This rank correlation analysis was applied to the total patient population for the following outcome measures and clinical group combinations: (1) clinical status vs. predose measurements; (2) response duration vs. predose measurements; (3) response duration (response duration >0) vs. predose measurements; (4) postdose TUNEL % vs. predose measurements; (5) clinical status vs. postdose measurements; (6) response duration vs. postdose measurements; (7) response duration (response duration >0) vs. postdose measurements; (8) Postdose TUNEL %–(response duration >0) vs. postdose measurements.

Analysis of Variance

Analysis of variance was employed to determine what measurement set variables, when grouped by outcome measures, were statistically distinct from each other, thus indicating that the measurement set variable may be able to discriminate between the posed outcome measures. To perform this analysis, a null hypothesis was formed using two independent sample sets. The sample sets were formed by grouping a superset by an outcome measure to form the two subsets. The null hypothesis was that the populations generating the two sample sets were identical. The significance of the null hypothesis was tested using non-parametric measures, specifically the Wilcoxon rank sum one-way analysis of variance, and the Kruskal-wallis nonparametric one-way analysis of variance (ANOVE). If p (the measure of probability) is near zero, this casts doubt on the null hypothesis, and requires the alternative hypothesis that the medians of the groups are different to be considered likely with probability (1-p). These two ANOVA variants are non-parametric and do no make a Gaussian assumption.

This analysis was applied to the total patient population for the following outcome measures and measurement set combinations: (1) postdose TUNEL % vs. predose measurements; (2) clinical status (partial response vs. others)(predose measurements only); (3) clinical status (partial response vs. others)(postdose measurements only); (4) postdose TUNEL % (post treatment indication sets only); (5) clinical status (partial response and stable disease vs. progressive disease).

This analysis was also applied to the subpopulations of breast cancer and not breast cancer for the following outcome measures and measurement set combinations:

Not breast cancer: (1) postdose TUNEL % vs. predose and postdose measurements; (2) clinical status (PD vs. SD) predose and postdose measurements (note the number of PR=0 for not breast cancer subjects).

Breast Cancer: (1) Postdose (TUNEL %≦30 vs. TUNEL %>30), predose and postdose measurements; (2) clinical status (PR and SD vs PD) predose and postdose measurements; (3) clinical status (PR vs. SD) predose and postdose measurements (note PD excluded); (4) postdose (TUNEL %≦30 vs. TUNEL %>30) predose and postdose measurements (note: PD excluded); (5) clinical status (SD vs PD) predose and postdose measurements (note: PR excluded).

Receiver Operator Curve and Linear Discriminate Analysis

A Receiver Operator Curve (ROC) plot displays the achievable sensitivity and specificity for classifying an outcome into one of two classes. The ROC specifically plots 1-specificity (false positive rate) vs. sensitivity (true positive rate). The area under a ROC provides an indication of the degree two outcomes can be successfully classified. A high ROC AUC score indicates a good result, while an AUC of 0.5 indicates a random result.

Linear Discriminant techniques, introduced by Fisher have long been a standard technique in pattern classification, and may be used effectively to provide a small set of features that carry the most relevant information for classification purposes. LDA is also applicable to small data set problems (equivalently sparse dimensional representation problems). Linear discriminate analysis was performed to investigate the differences among the various outcome measures, to determine which measurement set variables discriminate between the respective outcome measure classes. Similar to analysis of variance for single variables, LDA examines the within-class variance and between-class variance to identify the differences between the classes. The result of LDA for a two-class problem is a linear projection from the multivariate input space to a one dimensional output space that is optimal for separating the classes in a linear sense. The advantage of this technique in this small sample set problem is its transparency and the implicit linear constraint for separating classes in the sparse data space.

Linear Discriminate analysis followed by ROC AUC scoring was applied to all interactions between predose measurements for the following outcome measures.
   Not breast cancer: (1) postdose TUNEL % vs. predose and postdose measurements; (2) clinical status (PS vs. SD) predose measurements (note: the number of PR=0 for not breast cancer subjects).
   Breast Cancer: (1) postdose TUNEL %≦30 vs. TUNEL %>30), predose measurements; (2) clinical status (PR and SD vs. PD), predose measurements.

Results

In these analyses, the division of data into 'Breast cancer only' and 'not breast cancer' was the most effective manner to identify the meaningful relationships. These groups are presented separately. Each marker is associate with its correlate significance or association for the selected data set (Breast Cancer only or Not Breast Cancer) based on pre-treatment and post-treatment values.

The significance of the marker in each subset of patients (Breast Cancer; Not Breast Cancer) is shown in Tables 6A, 6B, 7A and 7B. If there was no statistical support for a marker, "none" is indicated. Biomarker utility is provided in Tables 6A and 7A; statistical support is provided in Tables 6B and 7B.

Legend for Tables 2A, 2B, 3A, 3B:
   PR=clinical status Partial Response (PR) is discriminated from clinical status Stable Disease (SD) and Progressive Disease (PD)
   PD=clinical status Progressive Disease (PD) is discriminated from clinical status Stable Disease (SD) and Partial Response (PR)
   RD R=Correlation with Response Duration
   RD (RD>0)R=correlation with response duration for sub-population with response duration>0
   TR=correlation with postdose TUNEL %
   T(RD>0)R=correlation with post dose TUNEL % for sub-population with Response Duration>0
   NS=not statistically significant
   % C=percent change in measurement between postdose and predose
   Post=post dose measurement
   Post-pre=postdose measurement−predose measurement

TABLE 2A

Breast Cancer Only-significance of measurements with respect to clinical response

| Marker | Pre-treatment measure | Post-treatment measure |
|---|---|---|
| ErbB1 (EGFR) | None | None |
| pErbB1 | None | PD/response classifier and weak inverse response extent indicator |
| ErbB2 | Weak PR predictor | Weak PR indicator |
| pErbB2 | Moderate PR predictor | Weak PR indicator |
| pAKT | None | Moderate PR indicator and weak inverse response extent indicator |
| pERK | PD/Response predictor | PR indicator |
| PS6 | PR Predictor/weak predictor of response extent | Weak PR indicator, PD/response indicator |
| IGF-1R | PR predictor | Weak PR indicator, inverse correlation with postdose TUNEL in responders |
| TGFalpha | PR predictor/weak predictor of response extent | Weak PR indicator, inverse correlation with postdose TUNEL in responders |
| Cyclin D | None | None |
| TUNEL | Potential Exclusion criteria for PD | 1—1 correspondence PR indicator |

TABLE 2B

Breast Cancer Only (Statistics shown only for pS6, IGF-1R, TGFalpha, and TUNEL)

| | Pre-Treatment | Post-Treatment |
|---|---|---|
| pS6 | PR p < 0.05 AUC .98 (13) | Post PR p > 0.05 AUC .52 (14) |
| | PD p > 0.05 AUC .68 (13) | % C PR p > 0.05 AUC .82 (13) |
| | T (RD > 0) R .86 p < 0.05 | Post PD p < 0.05 AUC .86 (14) |
| | TR p > 0.05 | % C PD p > 0.05 AUC .68 (13) |
| | RD R p > 0.05 | RD R p > 0.05 |
| | RD (RD > 0) R p > 0.05 | RD (RD > 0) R p > 0.05 |
| | | T R p > 0.05; T (RD > 0) R p > 0.05 |
| IGF-1R | PR p < 0.05 AUC .98 (13) | Post PR p > 0.05 AUC .80 (14) |
| | PD p > 0.05 AUC .65 (13) | % C PR p = 0.09 AUC .88 (13) |
| | TR .58 p < 0.05 | Post PD p > 0.05 AUC .69 (14) |
| | T (RD > 0) R .64 p = .09 | % C PD p > 0.05 AUC .56 (13) |
| | RD R p > 0.05; RD (RD > 0) R p > 0.05 | % Change: T (RD > 0) R-.77 p < 0.05 |
| | | T R p > 0.05 |
| | | RD R p > 0.05; RD (RD > 0) R p > 0.05 |
| TGFalpha | PR p < 0.05 AUC .96 (14) | Post PR AUC .70 (15) |
| | PD p > 0.05 AUC .62 (14) | % C PR AUC .78 (14) |
| | T R p > 0.05 | Post PD AUC .80 (15) |

TABLE 2B-continued

Breast Cancer Only (Statistics shown only for pS6, IGF-1R, TGFalpha, and TUNEL)

| | Pre-Treatment | Post-Treatment |
|---|---|---|
| | T (RD > 0) R .75 p < 0.05<br>RD R p > 0.05; RD (RD > 0) R<br>p < 0.05 | % C PD AUC .62 (14)<br>% Change: T (RD > 0) R-.68 p < 0.05<br>Post-Pre: T (RD > 0) R-.73 p < 0.05<br>T R p < 0.05<br>RD R p < 0.05; RD (RD > 0) R p < 0.05<br>PR AUC 1 (15) |
| TUNEL | All patients with high postdose TUNEL % had some predose TUNEL % | Post dose TUNEL had 1—1 correspondence with PR |

TABLE 3A

Not Breast Cancer

| Marker | Pre-treatment measure | Post-treatment measure |
|---|---|---|
| ErbB1 (EGFR) | None | None |
| pErbB1 | None | None |
| ErbB2 | Weak PR predictor; PD predictor | Weak PD indicator |
| pErbB2 | Weak PR predictor; Weak PD predictor | None |
| pAKT | Weak PR predictor<br>Moderate PD predictor and indicator of extent of response for those whom respond | PR indicator<br>PD indicator |
| pERK | Weak PD predictor | NS |
| PS6 | Weak PD predictor | NS |
| IGF-1R | None | None |
| TGFalpha | None | PR indicator (inversely correlated with postdose TUNEL %)<br>Weak PD indicator |
| Cyclin D | None | None |
| TUNEL | All patients with high postdose TUNEL % had some predose TUNEL % | NS or trivial |

TABLE 3B

Not Breast Cancer (Statistics shown for pS6, IGF-1R, TGFalpha, TUNEL)

| | Pre-Treatment | Post-Treatment |
|---|---|---|
| pS6 | NS<br>PD p = 0.09<br>AUC 0.82 (18) | NS |
| IGF-1R | NS | NS |
| TGFalpha | NS | Post PD p = 0.06 AUC 0.83 (15)<br>% C PD p > 0.05 AUC 0.61 (14)<br>% C PR p < 0.05 AUC 1.0 (9)<br>Post PR p < 0.05 AUC 1.0 (10)<br>% C T R −0.79 p < o.o5<br>Post-Pre T R −0.68 p < 0.05<br>Post-pre RD (RD > 0) R 0.98<br>p < 0.01<br>T (RD > 0) R p > 0.05 |
| TUNEL | All patients with high postdose TUNEL % had some predose TUNEL % | Post-dose and change are trivial relationships by definition. |

Example 4

Effects of Lapatinib on Biomarkers in Clinical Tumor Biopsies

Forty-two percent of the patients on study were women with metastatic breast cancer, all previously treated with multiple chemotherapeutic regimens most in combination with trastuzumab. For purposes of this Example, "inhibition" of a biomarker refers to a decrease in the level of the biomarker, assessed by comparing the level detected in a Day 0 biopsy from a patient to the level detected in a Day 21 biopsy from the same patient.

Partial Response (PR) was observed in four patients, each patient with metastatic breast cancer whose disease had progressed despite multiple prior chemotherapies with and without trastuzumab, and in some cases with hormonal therapy.

In the four patients with PR, variable levels of inhibition were seen (FIGS. 1A-1F) in (i) p-ErbB1, (ii) p-ErbB2, (iii) p-Erk1/2, (iv) p-Akt, (v) cyclin D1, or (vi) combinations of these molecules. All four patients exhibiting PR were treated for breast cancer, including aggressive inflammatory breast cancer (IBC; 2 patients) and non-inflammatory metastatic breast cancer (2 patients).

Partial Response was seen in two patients with aggressive inflammatory breast cancers (IBC), whose tumors expressed high levels of ErbB1 and p-ErbB2 (prior to treatment). In the first patient with IBC, p-ErbB2 was inhibited 72%, resulting in p-Akt (90%) and cyclin D1 (49%) inhibition after 21 days of lapatinib (650 mg/d) (FIG. 1). A second patient with IBC who experienced PR, showed inhibition of p-ErbB1 (80%) and p-ErbB2 (83%), as well as inhibition of p-Erk1/2 (68%), and cyclin D1 (57%) (FIG. 1A, 1B, 1C, 1F, ■). This patient also experienced marked tumor regression despite p-Akt remaining essentially unchanged (FIG. 1D, ■)(Table 4)

In a patient with non-inflammatory metastatic breast cancer who exhibited Partial Response (PR) to 900 mg/day of lapatinib, p-ErbB1 was inhibited 31% while p-ErbB2 remained unchanged (FIG. 1A, 1B, v). Nevertheless, p-Erk1/2 was completely inhibited with marked inhibition of cyclin D1 (90%) and p-Akt (44%) (FIGS. 1A-1F, FIG. 2, v).

Figure 2:
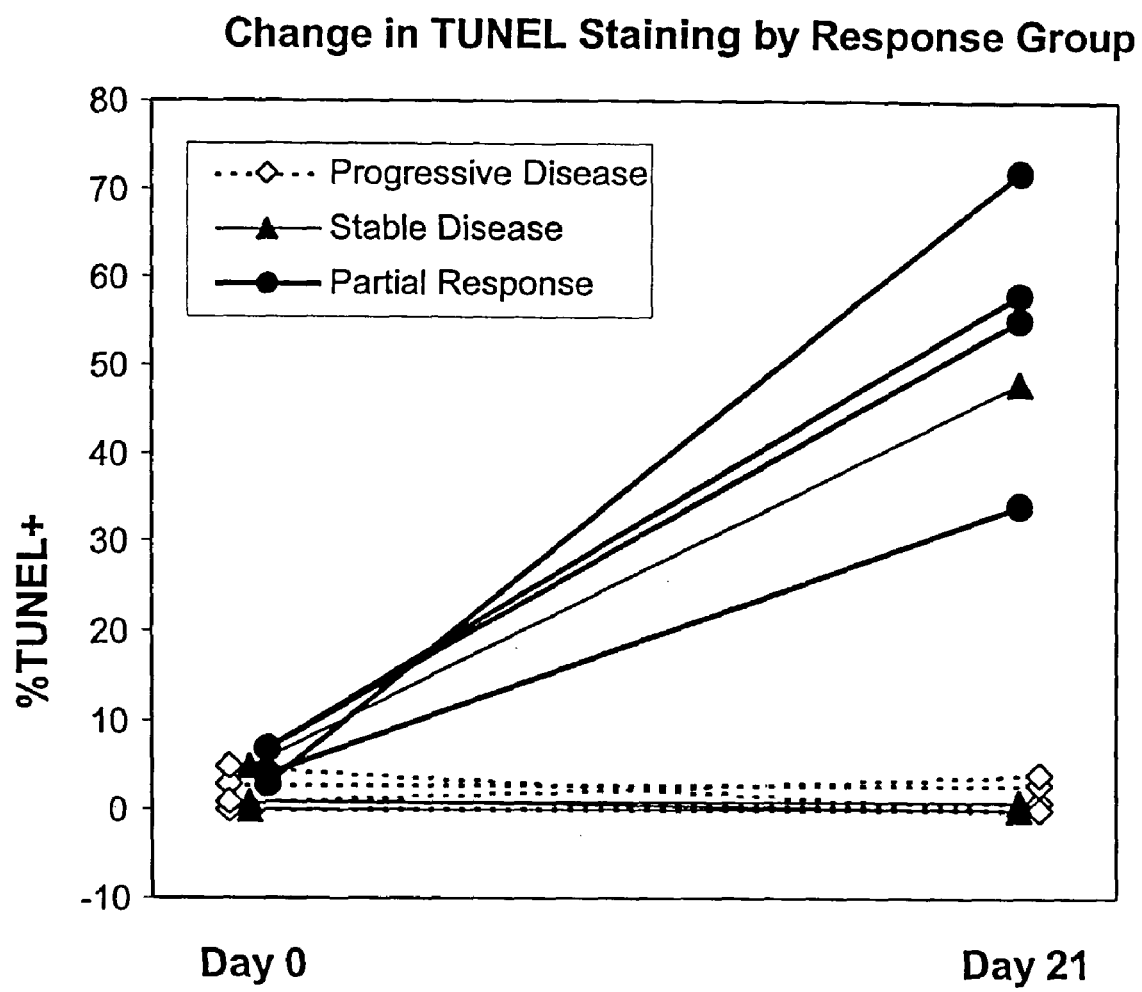
FIG. 2 charts change in TUNEL staining (% change) by response group, where Progressive Disease is indicated by a dashed line and open diamond, Stable Disease by a solid line and solid triangle, and Partial Response by a solid line and solid circle. TUNEL scores were assessed in tumor biopsy tissue obtained at Day 0 (prior to treatment with lapatinib) and at Day 21 after lapatinib treatment was started.

An additional patient who experienced PR, also with non-inflammatory metastatic breast cancer, expressed high levels of ErbB1 and ErbB2, and showed complete inhibition of p-Erk1/2 after 21 days of lapatinib (1200 mg/d), inhibition of cyclin D (90%), with less of an effect on p-Akt (34%) (FIG. 2, λ). Interestingly, this response was not associated with any appreciable inhibition of p-ErbB1 or p-ErbB2.

TABLE 4

Biological markers in in chemotherapy/hormone/Trastuzumab refractory Inflammatory Breast Cancer, treated with 900 mg/day Lapatinib, showing Partial Response (PR)

|  | ErbB1 | pErbB1 | ErbB2 | pErbB2 | pErk Index | Cyclin D | pAkt | TGFa | TUNEL |
|---|---|---|---|---|---|---|---|---|---|
| Day 0 | 35 | 5 | 70 | 29 | 2397 | 28 | 20 | 54 | 3 |
| Day 21 | 32 | 1 | 65 | 5 | 760 | 12 | 20 | 21 | 72 |
| % change | −9 | −80 | −7 | −83 | −68 | −57 | −0 | −61 | +2400 |

The present results suggest that although inhibition of p-ErbB2, p-ErbB1, MAPK-Erk1/2 and/or PI3K-Akt pathways may be necessary for achieving a clinical response, it may not be sufficient. In this context, a patient with breast cancer who exhibited PD after 8 weeks of therapy showed marked inhibition of p-ErbB1 (81%), p-Erk1/2 (87%) and cyclin D1 (76%), yet p-Akt was essential unchanged (FIG. 1, *) (Table 5) These results suggest that a non-ErbB pathway was mediating tumor survival in this particular patient. The fact that TUNEL score did not show an increase when measured in the Day 21 biopsy was consistent with the existence of a non-ErbB pathway.

TABLE 5

Biological markers in breast cancer, treated with 900 mg/day Lapatinib, showing negative clinical response (Progressive Disease)

|  | ErbB1 | pErbB1 | ErbB2 | pErbB2 | pErk Index | Cyclin D | pAkt | TGFa | TUNEL |
|---|---|---|---|---|---|---|---|---|---|
| Day 0 | 14 | 16 | 44 | 3 | 1081 | 42 | 36 | 49 | 0 |
| Day 21 | 19 | 3 | 32 | 3 | 0 | 10 | 33 | 23 | 0 |
| % change | +35 | −81 | −27 | 0 | −100 | −76 | −8 | −53 | 0 |

Example 5

Correlation of Biological and Clinical Response

In this study, increased TUNEL score in the Day 21 biopsy (compared to TUNEL score in the Day 0 biopsy) consistently differentiated lapatinib responders (SD, PR) from non-responders (PD)(FIG. 2). In prior cell-based assays, particularly in ErbB2 overexpressing breast cancer cell lines, lapatinib-induced apoptosis has been shown to occur at pharmacologically relevant concentrations (Xia et al., Oncogene 21:6255 (2002); Rusnak et al., Mol Cancer Ther 1:85 (2001); Koch et al., Eur J Cancer 1 (suppl 5): 559a, (2003)). For purposes of this Example, an "increase" in TUNEL score refers to an increased TUNEL score in the Day 21 biopsy, compared to the TUNEL score of the Day 0 biopsy from the same patient.

TUNEL staining is a quantitative measurement of DNA fragmentation characteristic of cellular apoptosis. The percentage of tumor cells that were stained positive by TUNEL markedly increased in Day 21 biopsy in all four patients achieving Partial Response (PR) (FIG. 2, solid line with solid circle). The TUNEL score increased in an additional patient with an ErbB1-overexpressing head and neck carcinoma who had radiographic evidence of tumor regression after 8 weeks of lapatinib therapy, though not sufficient to qualify as a PR. In contrast, TUNEL scores did not increase in any of the patients with PD at 8 weeks (FIG. 2, dashed line, open diamond).

All five patients showing Day 21 increase in TUNEL score had a Day 0 TUNEL score of greater than zero.

Example 6

Predictors of Response

The level of biomarker expression based on quantitative IHC (OD values) in pre-treatment tumor biopsies and the change between pre- and post-treatment values (see above Examples) were analyzed to determine whether a particular biomarker(s) was predictive of response or indicative of response in either breast or non-breast cancers.

The data was analyzed as subpopulations: only breast cancer and all non-breast cancers.

The data was analyzed to predict three outcomes: Clinical Outcome (PD, SD, PR); TUNEL score (Day 21 TUNEL score of >30), and Response Duration.

Tables 6 and 7 show those biomarkers from pre-treatment tumor biopsies that predict for clinical response in breast cancer (Table 7) and non-breast cancers (Table 6).

In breast cancers, pretreatment co-expression of IGF-IR and high p70S6 kinase predicted for positive clinical response in breast cancer. Day 21 TUNEL scores were highly correlative with response. Additionally, pre-treatment TUNEL score predicted for positive clinical response; none of the patients in this study with pre-treatment tumor TUNEL scores of 0 responded to lapatinib.

In non-breast cancers, whereas d 21 TUNEL scores were highly correlative with response, pre-treatment TUNEL score predicted for response; none of the patients in this study with pre-treatment tumor TUNEL scores of 0 responded to lapatinib.

TABLE 6

Predictors of Response in Non-Breast Cancers

| Assay | Predictor of | Statistics |
|---|---|---|
| TUNEL | Exclusion PR | All responders had Day 0 TUNEL > 0 |
| ErbB2 (pretreatment) | PD | Class. AUC ROC 0.8*; RD, 0.53* |
| pErbB2 | PR | Class. AUC ROC = 0.78; T, 0.71* |
| pAkt | PD | Class. AUC ROC 0.82** |
| pErk1/2 | PD | Class. AUC ROC 0.82 |
| P70S6K | PD | Class. AUC ROC 0.82 |
| NDF | PD | RD, −0.95** |

*p < 0.05
**p < 0.01

TABLE 7

Predictors of Response in Breast Cancers

| Assay | Predictor of | Statistics |
|---|---|---|
| TUNEL | Exclusion PR | All responders had Day 0 TUNEL > 0 |
| ErbB2 (pretreatment) | Exclusion PR | All responders had high Day 0 ErbB2 levels |
| pErbB2 | Exclusion PR | All responders had high Day 0 pErbB2 |
|  | PR | Class. AUC ROC = 0.84*; T, 0.76** |
| pErk1/2 | PD | Class. AUC ROC = 0.95**; RD, 0.62* |
| IGF-IR | PR | Class. AUC ROC = 0.98*; T, 0.58* |
| P70S6K | PR | Class. AUC ROC = 0.98*; T, 0.86* |
| TGFalpha | PR | Class AUC ROC = 0.96*; T, 0.75* |

*p < 0.05
**p < 0.01

That which is claimed is:

1. A method of screening a solid tumor as an aid in selecting anti-tumor therapy, comprising:
   (a) obtaining a pretreatment sample of tumor tissue;
   (b) measuring a biomarker selected from IGF-1R and pS6 in said tumor tissue to determine whether it is expressed at increased levels in the tumor tissue, and
   (c) correlating the measurement of increased pretreatment expression of said biomarker with an increased likelihood of a positive clinical response to treatment with a dual EGFR/ErbB2 inhibitor.

2. A method according to claim 1 where said EGFR/ErbB2 inhibitor is lapatinib.

3. A method according to claim 1 where said solid tumor is a breast cancer.

4. A method of screening a breast cancer tumor to determine suitability for treatment with lapatinib, comprising
   (a) obtaining a pretreatment sample of breast cancer tumor tissue;
   (b) measuring a biomarker selected from IGF-1R and pS6 in said tumor tissue to determine whether it is expressed at increased levels in the tumor tissue, and
   (c) correlating the measurement of increased pretreatment expression of said biomarker with an increased likelihood of a positive clinical response to treatment with lapatinib.

* * * * *